(12) United States Patent
Brown et al.

(10) Patent No.: US 7,482,502 B2
(45) Date of Patent: Jan. 27, 2009

(54) PROCESS FOR CRACKING HYDROCARBONS USING IMPROVED FURNACE REACTOR TUBES

(75) Inventors: David J. Brown, Houston, TX (US); Martyn D. Roberts, Houston, TX (US)

(73) Assignee: Stone & Webster Process Technology, Inc., Houston, TX (US)

( * ) Notice: Subject to any disclaimer, the term of this patent is extended or adjusted under 35 U.S.C. 154(b) by 601 days.

(21) Appl. No.: 10/350,685

(22) Filed: Jan. 24, 2003

(65) Prior Publication Data

US 2004/0147794 A1    Jul. 29, 2004

(51) Int. Cl.
C07C 4/04 (2006.01)
(52) U.S. Cl. ............... 585/652; 585/920; 585/922
(58) Field of Classification Search ............ 585/652, 585/920, 922
See application file for complete search history.

(56) References Cited

U.S. PATENT DOCUMENTS

| | | | |
|---|---|---|---|
| 2,018,619 A | 10/1935 | Winkler et al. | |
| 2,987,382 A | 6/1961 | Endter et al. | |
| 3,407,789 A | 10/1968 | Hallee et al. | |
| 3,671,198 A | 6/1972 | Wallace | |
| 4,342,642 A | 8/1982 | Bauer et al. | |
| 4,346,049 A | 8/1982 | Coppola et al. | |
| 4,412,975 A | 11/1983 | Parizot et al. | |
| 4,499,055 A | 2/1985 | DiNicolantonio et al. | |
| 4,647,304 A | 3/1987 | Petkovic-Luton et al. | |
| 5,206,880 A | 4/1993 | Olsson | |
| 5,254,318 A | 10/1993 | Williams et al. | |
| 5,427,655 A | 6/1995 | Woebcke et al. | |
| 5,630,887 A | 5/1997 | Benum et al. | |
| 6,111,156 A * | 8/2000 | Oballa et al. ............... | 585/330 |
| 6,139,649 A | 10/2000 | Wynns | |
| 6,312,652 B1 | 11/2001 | Duncan | |
| 6,383,455 B1 | 5/2002 | Duncan et al. | |
| 6,409,847 B2 | 6/2002 | Kleemann | |
| 6,475,647 B1 | 11/2002 | Mendez Acevedo et al. | |
| 6,514,631 B1 | 2/2003 | Yamamoto et al. | |

FOREIGN PATENT DOCUMENTS

| | | |
|---|---|---|
| EP | 0 564 665 B1 | 9/1997 |
| EP | 1018563 A1 | 7/2000 |
| JP | 10-27773 A | 10/1998 |
| JP | 11-63853 A | 3/1999 |

(Continued)

OTHER PUBLICATIONS

Lyle F. Albright, Comments on "Kinetic Modeling of Coke Formation during Cracking, Inds. & Engineering Chemistry Research," (2002) 41 (24), 6210-12.

(Continued)

*Primary Examiner*—Thuan Dinh Dang
(74) *Attorney, Agent, or Firm*—Locke Lord Bissell & Liddell LLP; Alan B. Clement

(57) ABSTRACT

The present invention discloses a process for cracking a hydrocarbon feedstock into olefinic hydrocarbon products in a furnace at a temperature of above about 1300° F. in a reactor furnace tube comprising a plurality of reaction lines constructed of a temperature-resistant, non-nickel containing material.

27 Claims, 10 Drawing Sheets

FOREIGN PATENT DOCUMENTS

| | | |
|---|---|---|
| JP | 11-209850 A | 8/1999 |
| WO | WO 99/09230 A1 | 2/1999 |

OTHER PUBLICATIONS

Marie-Francoise S.G. Reyniers, Sandra Wauters & Guy B. Marin, Reply to Comments on "Kinetic Modeling of Coke Formation during Steam Cracking," (Cont.) Industrial & Engineering Chemistry Research, (2002) 41 (24), 6213-14.

C.S. Tassen et al., "High Temperature Service Experience and Corrosion Resistance for Mechanically Alloyed ODS Alloys," Sep. 23-26, 1991.

K. Pham, D. Duncan and J. Gondolfe, Coke Free Cracking—Is It Possible, Tenth Ethylene Producers Conference, 1998.

R.H. Kane, G.M. McColvin, T.J. Kelly, J.M. Davidson, Incoloy Alloy MA 956-A Material for Advanced Ethylene Production Processes, Corrosion 84 Forum Paper No. 12, Apr. 26, 1984.

* cited by examiner

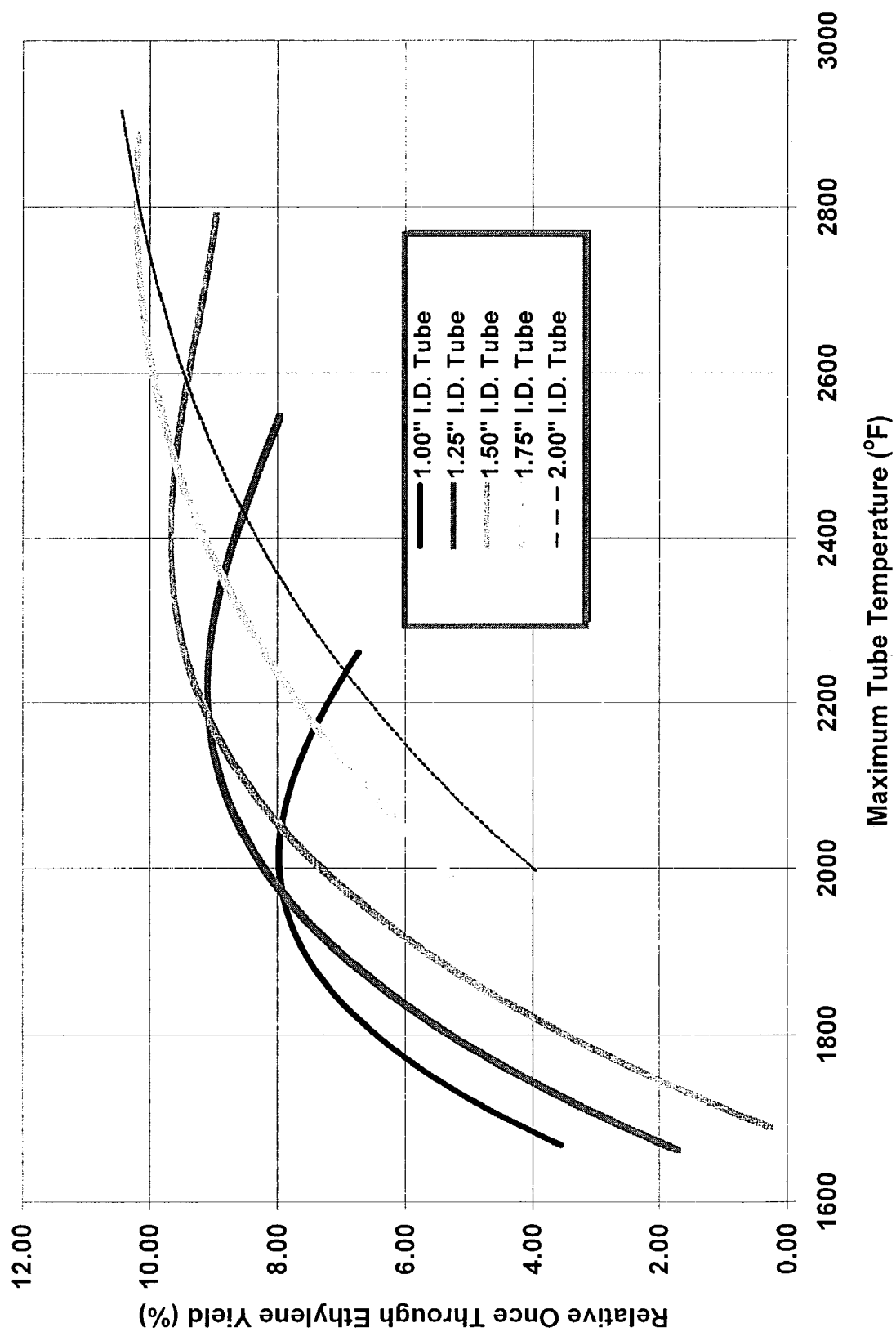

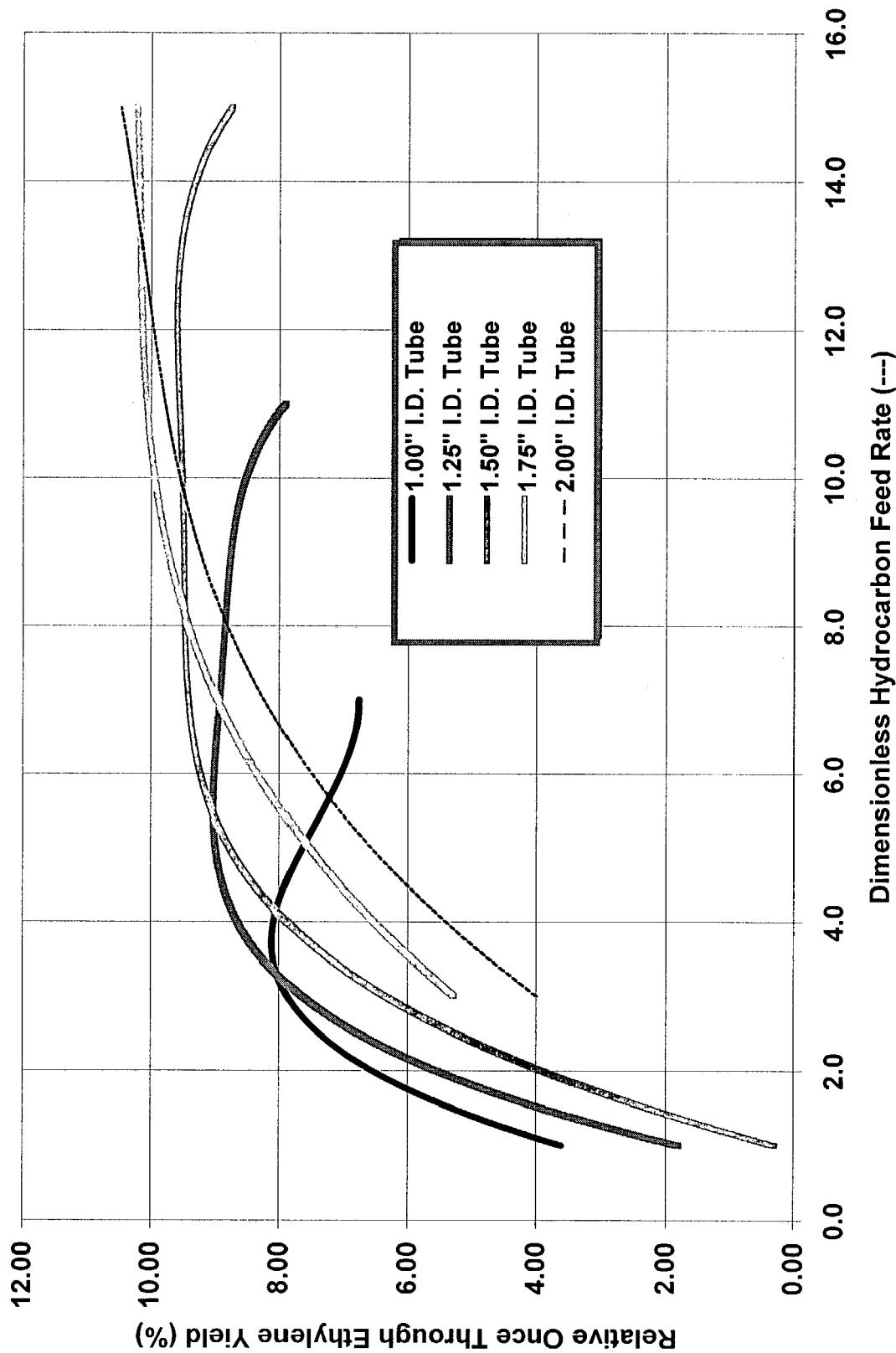

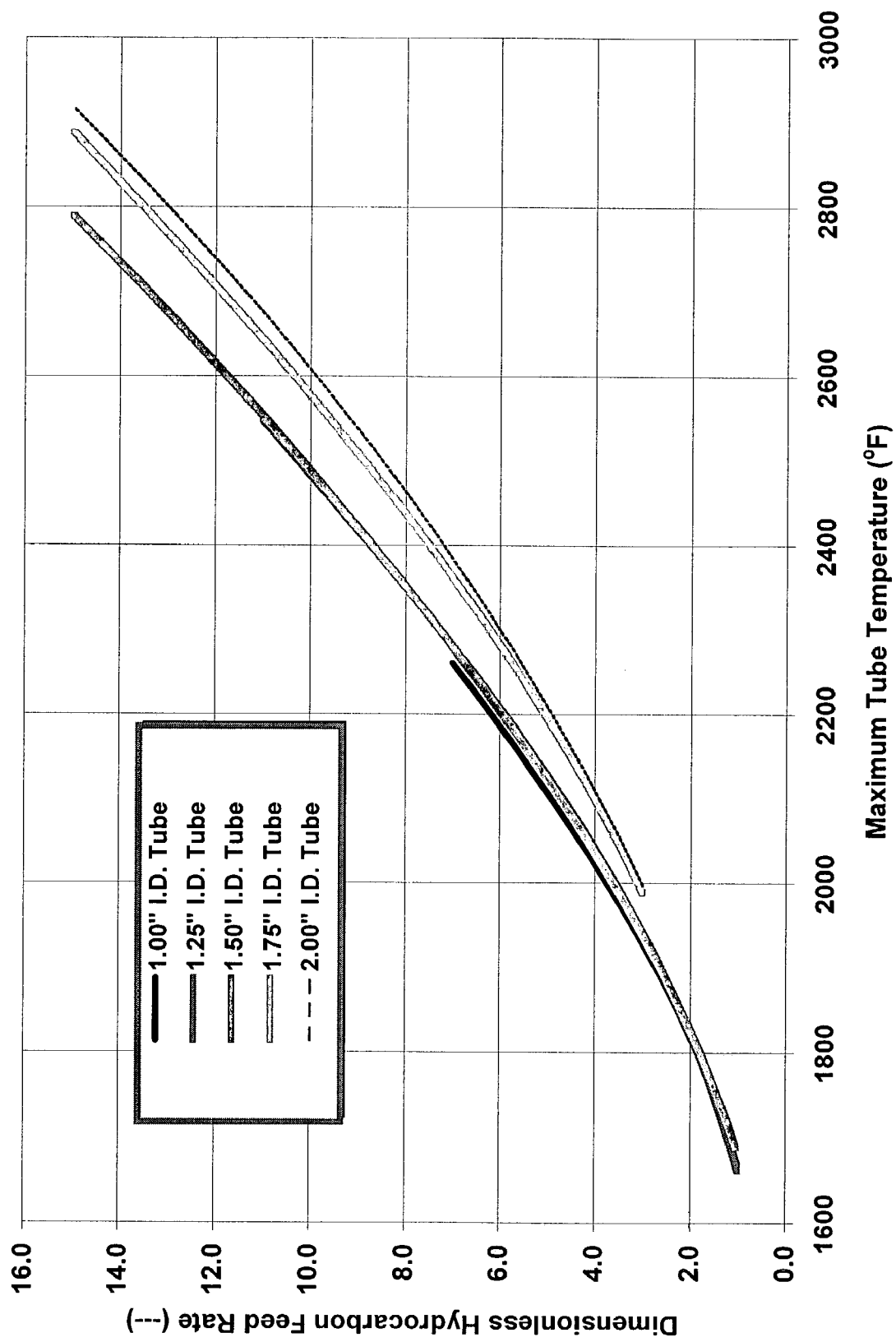
FIG. 8 Performance Parameters III

PROCESS FOR CRACKING HYDROCARBONS USING IMPROVED FURNACE REACTOR TUBES

FIELD OF THE PRESENT INVENTION

The present invention relates to a process using improved reactor tubes for use as a heat-absorbing surface in any fired heater or furnace. More specifically, the present invention relates to a process for cracking hydrocarbons to produce olefinic gases (a process also known as 'pyrolysis') using improved reactor furnace tubes, such as by reducing the catalytic coking that occurs with the use of conventional tubes, and at the same time, significantly improving product yields. Most specifically, the present invention relates to the use of high-performance reactor furnace tubes comprised of ceramic and/or oxide dispersion-strengthened ("ODS") materials in the process of cracking of hydrocarbons by pyrolysis at significantly higher reactor furnace tube temperatures than previously practiced.

BACKGROUND OF THE PRESENT INVENTION

Cracking furnaces long have been used in the process of cracking a variety of hydrocarbon feedstocks to ethylene and other valuable olefinic gases. For the past 20 or 30 years, pyrolysis cracking at relatively short residence times and relatively high temperatures in furnace reactors has been the favored process for the production of ethylene, which is used as a precursor for several kinds of plastics (e.g., polyethylene, polystyrene, and PVC) and other everyday items such as ethylene-glycol (antifreeze). U.S. Pat. Nos. 2,671,198; 3,407, 789; 3,671,198; 4,342,642; 4,499,055 and 5,427,655 illustrate basic designs of such short-residence time/high temperature cracking furnaces.

When thermally cracking saturated hydrocarbons to olefinic hydrocarbons—such as the cracking of ethane to predominantly ethylene, or the cracking of heavier saturated hydrocarbons like those comprising a naphtha or gas oil feedstock to produce less saturated products, such as ethylene and other higher olefins—it is generally desirable to input that quantity of heat needed to effect cracking of the hydrocarbon feed very rapidly while reducing the time that the initial cracking product is exposed to the cracking heat in order to increase the selectivity of such cracking conversion. It is this concept that underlies the millisecond residence time at a high temperature that is now the preferred process for furnace cracking of hydrocarbon feeds.

The cracking furnace used in the cracking process is any directly fired device in which a hydrocarbon feed, in the presence of dilution steam, passes through reactor furnace tubes in which endothermic reactions take place to form a wide range of cracked products, including ethylene. A conventional cracking furnace generally comprises a refractory lined firebox containing a multiplicity of high alloy metal reactor furnace tubes through the interior of which flows the hydrocarbon feedstock to be cracked, together with a suitable amount of dilution steam. The sensible heat and the heat of cracking are supplied primarily by radiant heat from burners located on the floor and/or walls of the firebox. This heat transfers through the metallic reaction lines (reactor furnace tubes) into hydrocarbon feedstock that flows there within. A reaction line may be as long as 400 feet and/or coiled in a serpentine shape that runs vertically up and down in the firebox, or it may be as short as about 50 feet in a straight single pass through the firebox, with or without a 'crank' (see DiNicolantonio et al., U.S. Pat. No. 4,499,055; Wallace, U.S. Pat. No. 3,671,198; Parizot et al., U.S. Pat. No. 4,412,975). Intermediate lengths and other geometrical configurations also are possible and, indeed, currently practiced.

Cracking furnaces, as constructed today, provide for millisecond residence time at a maximum bulk fluid temperature of about 1625° F., and are, with respect to their radiant heated reactor furnace tubes, constructed of metallic materials. The fireboxes themselves, which may be lined with refractory materials, are capable of delivering a greater heat load than the metallic materials of the reactor furnace tubes can withstand. This maximum service temperature of the metallic materials, of which the reactor furnace tubes are constructed, limits the performance of the aforesaid reactor furnace tubes with regard to their capacity (which should be as high as possible), and their residence time (which should be as short as possible), and hence selectivity (to achieve the highest possible yield of valuable olefinic species like ethylene and propylene, for example).

To date, given the relatively high temperatures to which the reactor furnace tubes are exposed in a thermal cracking process, metallic materials have been preferred as the only materials for construction of such tubes. As reactor designers have strived for the higher capacity and higher selectivity in the process, which would result from the use of materials with higher maximum service temperature limits, they have steadily improved the properties of the metallic alloys from which the reactor furnace tubes are manufactured. In recent times, conventional reactor furnace tubes have been constructed of nickel-containing alloys. In general, the development of the nickel-containing alloys for reactor furnace tubes, in order to increase the maximum service temperature of the aforesaid reactor furnace tubes, has been accomplished by the addition of ever-increasing amounts of nickel. See, for example, Kleeman, U.S. Pat. No. 6,409,847. The best nickel-based alloys, however, still have maximum service temperatures of only around 2100° F. The exposure of conventional reactor furnace tubes to additional high temperatures will exacerbate the problems already existent with conventional reactor furnace tubes, which include, but are not limited to, accelerated coke formation, consequential carburization and creep elongation.

At high cracking temperatures, the nickel in conventional reactor furnace tubes acts as a catalyst for coke formation inside the line—a particular form of coke that is termed "catalytic coke." Coke also forms on the walls of the metal lines as the result of the pyrolysis itself, i.e., the action of time and temperature (particularly the very hot wall temperature) on the coke precursor material produced in the reactant mass. This type of coke, having both a different formation mechanism and a different structure from catalytic coke, is known as "pyrolytic coke." The coke formed by pyrolysis overlays on top of the catalytic coke in the reactor furnace tube. The pyrolytic coke, being a function of time, temperature and coke precursor material, increases in amount along the line length, peaking at the output end of the reaction line where time, temperature and precursors are at increased levels. For a recent example of a general discussion of cokeformation in the cracking field, see, for example, the following: *Kinetic Modeling of Coke Formation during Steam Cracking*, S. Wauters and G. B. Marin, Industrial & Engineering Chemistry Research, 41 (10), 2379-91; *Comments on "Kinetic Modeling of Coke Formation during Steam Cracking,"* Lyle F. Albright, Industrial & Engineering Chemistry Research, 41 (24), 6210-12; and *Reply to Comments on "Kinetic Modeling of Coke Formation during Steam Cracking,"* Marie-Françoise S. G. Reyniers, Sandra Wauters, and Guy B. Marin, Industrial & Engineering Chemistry Research, 41 (24), 6213-14.

Coke formation is deleterious to the process for a number of reasons. The deposition of coke on the insides of the reactor furnace tubes constricts the flow path for the hydrocarbons, causing an increased system pressure drop. The higher average hydrocarbon partial pressure reduces the selectivity of the process; and in extreme cases, the coke can cause maldistribution of flow (between parallel reactor furnace tubes) and, ultimately, a decrease in the furnace capacity. Additionally, the coke lay-down on the inside of the furnace tubes increases the resistance to heat transfer between the outside of the reactor tube wall and the bulk fluid flowing within the reactor tube. Consequently, the outside flue gas temperature, the firing rate and the outside tube wall temperature have to be increased in order to maintain the same temperature and/or conversion of the hydrocarbon fluid flowing within the tube. Eventually the outside temperature of the wall of the reactor tube can reach the maximum service limit for the material from which the tube is manufactured, under which circumstances the coke has to be removed by passing a mixture of steam and air through the tubes in order to convert the coke (basically carbon) to a mixture of carbon oxides. This process is known as "decoking." Decoking consumes valuable resources and, in the case of conventional nickel-based metallic alloy reactor furnace tubes, reduces the life of the tubes. Tube life is reduced by a variety of mechanisms including, but not limited to, abrasion, thermal fatigue, and damage to the internal oxide protective layer.

By way of example, in the process of ethane cracking, generally the coke precursor material with the highest rate of coking from pyrolysis is acetylene, although species such as ethylene, butadiene, and benzene also contribute to the coking. Coke produced by catalyzed reaction on the nickel in the tubes, on the other hand, can be formed from almost any hydrocarbon and, of course, at lower temperature levels and in less time than needed for pyrolytic coke.

In order to reduce catalytic coking in alloy reaction lines, those skilled in the art have employed a variety of means. For instance, sulfur dosing and chemical treatments have been used to suppress catalyst sites by cladding and bonding. Other surface treatments have been employed, such as coatings and vapor deposition of ceramic based chemicals. Benum et al., U.S. Pat. No. 5,630,887, describes a method for treating for furnace tubes to reduce carburization or coking. Similarly, Wynns, U.S. Pat. No. 6,139,649, describes a method for coating high temperature nickel chromium alloy products such as furnace tubes to reduce coking. Additionally, Mendez Acevedo et al., U.S. Pat. No. 6,475,647, describes a protective coating system for protecting stainless steel from coking and corrosion.

In addition, dilution steam is often used to reduce coke formation inside the lines and to lower hydrocarbon partial pressure to provide improved ethylene yields (selectivity). The use of dilution steam, however, also significantly increases the cost and complexity of operation by adding the need for steam-raising equipment and by reducing the reactor throughput resulting in expensive and cumbersome downstream operations to separate the water from the hydrocarbon products.

Despite such efforts, coking in the high temperature region of the reaction line continues, run lengths remain short and furnace shutdown is common.

Attempts to reduce coking by varying the materials used for reactor furnace tubes are found in the prior art. For example, the prior art describes the use of silicon ceramics for reactor furnace tube construction. For example, Winkler et al., U.S. Pat. No. 2,018,619, describes an apparatus for the pyrogenic conversion of hydrocarbons that uses reaction lines made from silicon powder; Endter et al., U.S. Pat. No. 2,987,382, describes a furnace for carrying out gas reactions in ceramic tubes; Coppola et al., U.S. Pat. No. 4,346,049, discloses silicon carbide powder compacts produced from alpha phase silicon carbide powder for forming furnace lines; and Williams et al., U.S. Pat. No. 5,254,318 describes lined tubes for high pressure reformer reactors. However, none of these references teach or suggest the improvements in the cracking process that are possible when using ceramic or ODS tubes at significantly higher temperatures than conventionally employed.

Additionally, European Patent Application EP 1 018 563 A1 discloses a heating furnace tube comprising a rare earth oxide particle dispersion iron alloy containing 17-26 wt. % of Cr and 2-6 wt. % of Al and a method for using and manufacturing such a heating line in locations where the coking and carburization problems occur during the process. Although, EP '563 briefly mentions that the entire tube can be constructed of the rare earth oxide particle dispersion iron alloy, at page 6, lines 42-45, the patentees specifically state that it is advisable to use the material only for tube portions where coking problems occur. Thus, EP '563 clearly teaches away from any benefit to the cracking process of constructing the entire tube of from the alloy. EP '563 also does not suggest in any way that the two characteristics of rare earth oxide particle dispersion iron alloy—being nickel-free and having a high maximum service temperature—can be used to produce a furnace reactor tube in which hydrocarbons can be processed and cracked at higher capacity, shorter residence time, higher selectivity and, under some circumstances, higher conversion than possible heretofore.

Finally, Tassen, C. S. and co-workers, in a paper entitled "High Temperature Service Experience and Corrosion Resistance for Mechanically Alloyed ODS Alloys," Heat-Resistant Materials, Proceedings of the First International Conference, Fontana, Wis., 23-26 Sep., 1991, suggest that ". . . MA alloys should perform exceptionally well in . . . pyrolysis and steam methane reforming atmospheres . . . ." The assertion is, however, made entirely in the context of the superior carburization resistance of MA ODS (mechanical alloyed oxide dispersion strengthened) alloys. The paper does not teach or suggest in any way that ODS alloys reduce the formation of coke. Neither does the paper teach or suggest in any way that the two characteristics of rare earth oxide particle dispersion iron alloy—being nickel-free and having a high maximum service temperature—can be used to produce a furnace reactor tube in which hydrocarbons can be processed and cracked at higher capacity, shorter residence time, higher selectivity and, under some circumstances, higher conversion than possible heretofore.

Thus, while such prior art generally teaches the use of non-conventional reactor furnace tubes for reducing coking, the prior art does not teach or suggest that any benefit could be derived from a process for cracking a hydrocarbon feedstock into olefinic hydrocarbon products comprising cracking said hydrocarbons in a furnace at a temperature of above about 1300° F. in a reactor furnace tube assembly comprising at least one reactor furnace tube comprised of a temperature-resistant, non-nickel containing material.

Special mention is also made of Duncan et al., U.S. Pat. No. 6,383,455, and Duncan, U.S. Pat. No. 6,312,652, both of which disclose non-conventional reactors comprising ceramic components. Additionally, at the Eleventh Ethylene Forum on May 14-16, 1997 and at the 10$^{th}$ Ethylene Producers Conference in 1998, Messrs. Pham, Duncan and Gondolfe presented papers entitled "Emerging Technology: Ultra-High Conversion Steam Cracking for Ethylene Production Using Advanced Ceramics" and "Coke Free Cracking—Is It Possible," respectively, which discussed investigations into the use of ceramics for ethylene furnaces, but did not disclose or teach that improvements in ethylene production were possible by operating a furnace at high temperatures with non-nickel containing high-temperature resistant reactor tube materials.

SUMMARY OF THE PRESENT INVENTION

The present invention concerns an improved process for cracking a hydrocarbon feedstock in a furnace at significantly higher temperatures than previously employed in the art.

It is an object of the present invention to provide a process for cracking hydrocarbons to produce olefinic gases utilizing reactor furnace tubes that can reduce and/or substantially eliminate the catalytic coking that occurs with the use of conventional tubes and, at the same, time operate at significantly higher temperatures than can conventional tubes.

It is another object of the present invention to provide a process for cracking hydrocarbons utilizing reactor furnace tubes made of non-nickel containing high-temperature resistant materials.

It is still another object of the present invention to provide a process utilizing reactor furnace tubes that inhibit coking and are carburization and oxidation resistant with high flexure strength.

It is still a further object of the present invention to provide a process utilizing reactor furnace tubes that can withstand very high loads, in very short residence times, provide highly selective yields, and in the special case of ethane cracking, provide ultra-high conversion and longer run-length.

It is a further objective of the present invention to provide a process that allows a pyrolytic cracking process to be conducted at higher reactor furnace tube outer skin temperatures (up to about 2700° F. vs. metallic limit of 2100° F.), preferably without increasing the formation of catalytic coke inside the tubes.

It is a further another object of the present invention to provide a more cost efficient pyrolytic cracking process by utilizing furnace reactor tubes that can operate at higher capacity than conventional tubes and thereby facilitate the use of smaller and cheaper furnaces.

It is still further another object of the present invention to provide a more cost efficient pyrolytic cracking process by utilizing furnace reactor tubes that require less feedstock than conventional tubes to produce a given amount of product.

It is yet another object of the present invention to provide a process that allows cracking without the more costly use of dilution steam.

It is yet a further object of the present invention to provide a process that reduces the need to recycle large amounts of gas and reduces $CO/CO_2$ emissions. (In cracking ethane or propane at low and moderate conversions in conventional reactor furnace tubes, a large amount of unconverted gas needs to be separated from the product stream and recycled back to the furnace for cracking.)

It is yet another object of the present invention to provide an improved process for cracking ethane at very high conversions to produce improved ethylene yields.

These and other objects are achieved by the present invention, which relates to a process for cracking a hydrocarbon feedstock into olefinic hydrocarbon products, the process comprising cracking said hydrocarbons in a furnace at a reaction outlet temperature of above about 1300° F., preferably above about 1450° F., more preferably above about 1600° F., in a reactor furnace tube assembly comprising a plurality of reaction lines wherein at least one said reactor furnace tube is comprised of a temperature-resistant, non-nickel containing material.

BRIEF DESCRIPTION OF THE DRAWINGS

FIGS. 6-8 depict in chart form results of a parametric study.

DETAILED DESCRIPTION OF THE PRESENT INVENTION

The following detailed description of present invention is presented to illustrate the present invention and is not to be construed to limit the scope of the appended claims in any manner whatsoever.

Figure 1:
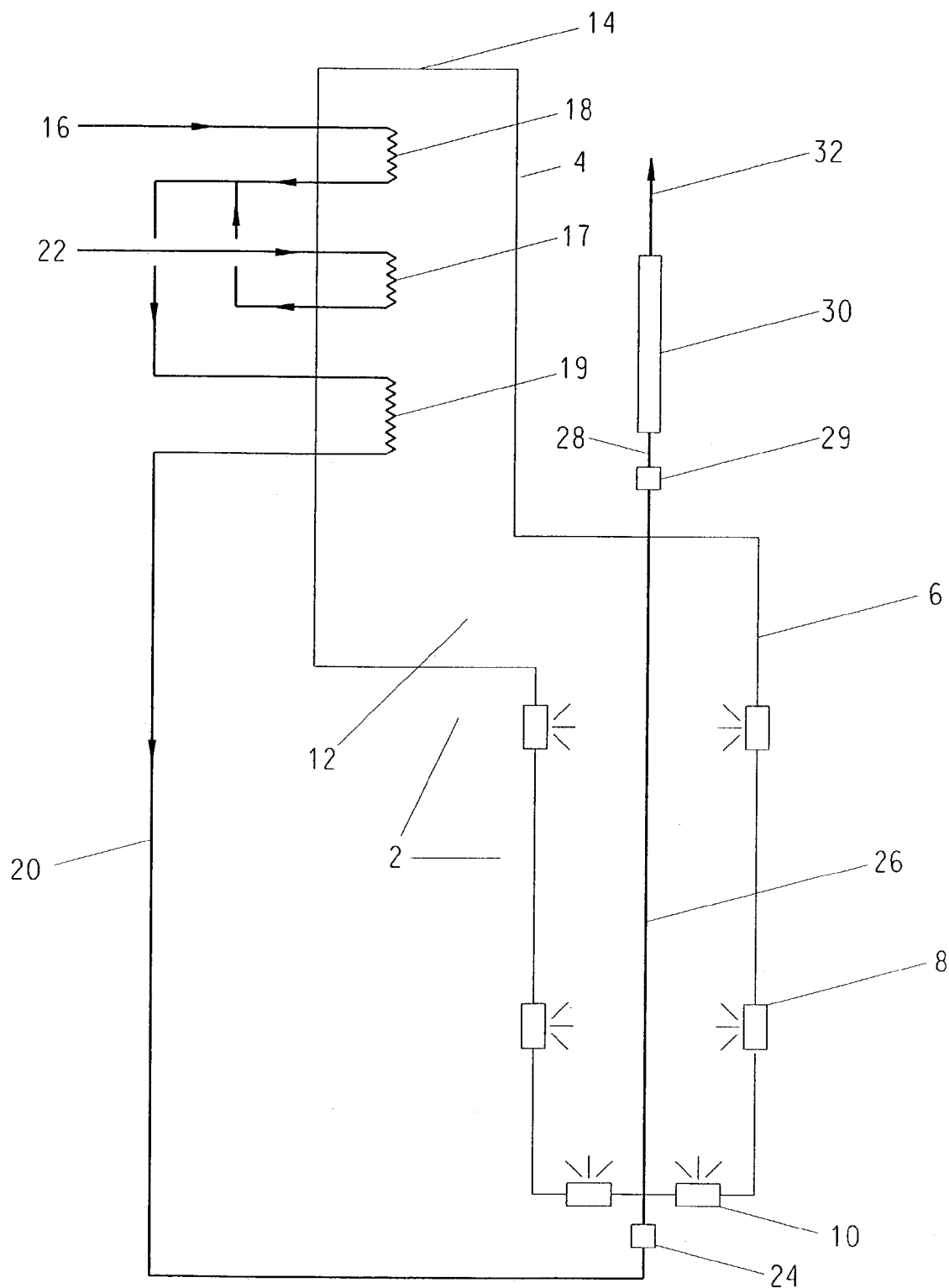
FIG. 1 depicts in schematic form an embodiment of a cracking furnace useful in the practice of the present invention.

FIG. 1 depicts in schematic form a cracking furnace 2 useful in the practice of the present invention. The furnace 2 comprises a preheat convection section 4 and a radiant section 6. The radiant section 6 is provided with wall burners 8 and floor burners 10, which are supplied with fuel via fuel lines (not shown). Of course, the furnaces of the present invention may comprise only wall burners, only floor burners or combinations thereof and are present in numbers sufficient to provide sufficient radiant heat for effecting the cracking reaction. The hot combusted gases produced by the burners exit the radiant section 6 of the furnace 2 via a transition flue 12, proceed upwardly through convection section 4 and exit the furnace via a flue 14.

In the process of the present invention, the feedstock enters the convection section 4 of the furnace through the feed line 16 and is preheated in a first exchanger (also known as a convection bank or convection bundle) 18 to a temperature ranging from about 200° F. to about 1000° F. Dilution steam enters the convection section 4 through a separate feed line 22 and is preheated in a second exchanger 17 to a temperature ranging from about 700° F. to about 1200° F. The preheated feed and preheated dilution steam are then mixed together and re-enter the convection section 4 into a third exchanger 19 in which the two admixed streams are heated to a temperature ranging from about 900° F. to about 1450° F. The mixture in a line 20 (commonly referred to as the crossover) is then directed to the radiant section 6 of the furnace 2. Alternative arrangements include, but are not limited to, the total elimination of dilution steam, in which case the feed goes directly from exchanger 18 to line 20 and exchangers 17 and 19, and separate feed line 22, are not required; or the feed is not preheated, in which case the feed in line 16 mixes directly with the preheated dilution steam from the exchanger 17 and exchanger 18 is eliminated. The crossover 20 to this point is comprised of conventional metallic materials, as are well known to those skilled in the art.

The feedstocks to the pyrolytic furnaces of the present invention can include any of those generally cracked in the art such as, but not limited to, propane, butane, naphtha, gas oils, or any combinations of any of the foregoing, in order to produce less saturated products such as ethylene and other higher olefins. A furnace reactor tube which has such a high resistance to coke formation would also be particularly effective for cracking heavy feeds like, for example, vacuum gas oil. Especially preferred is the pyrolytic process for selectively cracking ethane to ethylene by use of the process of the present invention by which, for example, ethane conversion can be improved from the 65% to 75% range of conventional furnaces to significantly higher levels, such as on the order of from about 85% to about 90%.

Joint 24 is between dissimilar materials. The reactor furnace tubes 26 of the present invention are entirely comprised of a high strength, oxidation resistant, carburization resistant, high-temperature resistant, non-nickel-containing material. Preferred such materials are ceramics or oxide dispersion strengthened materials.

The ceramic materials useful in the process of the present invention for preparing the reactor furnace tubes 26 are any of the known ceramic materials that can be shaped into a tubular construction and include, but are not limited to, silicon-carbide materials such as a direct sintered silicon-carbide (typically abbreviated DSSiC, DSSC, alpha and beta bond phases). Examples of DSSiC tubes include, but are not limited to, tubes sold under the trade name Hexoloy® SA by Saint-Gobain Advanced Ceramics (formerly Carborundum) and tubes sold under the trade name Halsic-S by W. Haldenwanger Technische Keramik GmbH & Co. KG. Further, the reactor furnace tubes 26 may be constructed of a wide variety of other SiC-based ceramic materials including, by way of example, materials taken from the group consisting of alpha silicon carbide, reaction bonded silicon carbide, silicon nitride, alumina, alumina/silicon carbide composites and composites based on silicon carbide. In addition, other useful ceramic materials may present themselves to those skilled in the art. See, for example, Jones, Divakar et al., U.S. Pat. No. 5,589,428; Tenhover et al., U.S. Pat. No. 5,616,426; Divakar et al., U.S. Pat. No. 5,635,430; and Eiermann, U.S. Pat. No. 5,813,845. Other families of ceramic materials useful in the preparing the reactor furnace tubes 26 of the present invention can be found at the web site having the URL address of http://www.scprobond.com/tech_corner.asp, wherein an excerpt of Metzger et al., "Understanding Silicon Carbide Types—Having the Right Tool for the Job" from the February 2000 issue of World Coal Magazine is reprinted.

Another useful material for constructing reactor furnace tubes in accordance with the present invention is what is commonly known as oxide dispersion strengthened materials or ODS materials. An exemplary ODS material useful in the practice of the present invention is a rare earth oxide dispersion strengthened ferrous alloy sold under the trade name Super Alloy Incoloy® MA956 by Special Metals Corporation; a virtually equivalent material is sold under the trade name PM 2000 by Plansee. However, the reactor furnace tubes 26 may be constructed of a wide variety of other useful ODS materials including, by way of example, a rare earth oxide dispersion strengthened ferrous alloy which contains from about 17% to about 26% of Cr by weight and about 2% to about 6% of Al by weight. In addition, other useful ODS materials may suggest themselves to those skilled in the art in light of the present description. Non-limiting descriptions of ODS materials useful in the practice of the present invention can be found in an article by I. G. Wright, C. G. McKamey, B. A. Pint and P. J. Maziasz of Oak Ridge National Laboratory entitled "ODS Alloys for High-Temperature Applications" and in Yamamoto et al., European Patent Application No. EP 1 018 563 A1.

The use of the high strength non-nickel containing materials as the material of construction for the entire length of the reactor furnace tubes of the present invention enables the cracking process to be run at significantly higher temperatures than practiced conventionally. For example, whereas conventional cracking in furnace tubes was generally limited to a outside tube skin temperature of at most about 2100° F., in the practice of the present invention, with the use of a tube constructed of the ODS materials, the outside tube skin temperature can be at least about 2300° F. Even higher outside tube skin temperatures can be employed where the tube is constructed of ceramic materials in accordance with the present invention, i.e., such as up to about 2900° F.

Figure 5A:
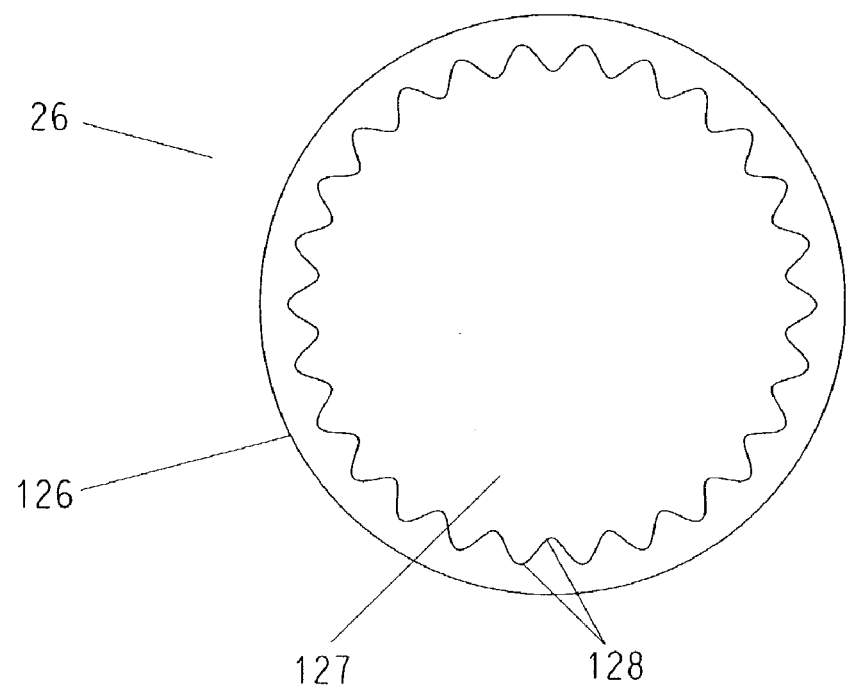
FIG. 5A depicts in cross-sectional form an embodiment of an internally finned tube for use in preferred embodiments of the present invention.
Figure 5B:
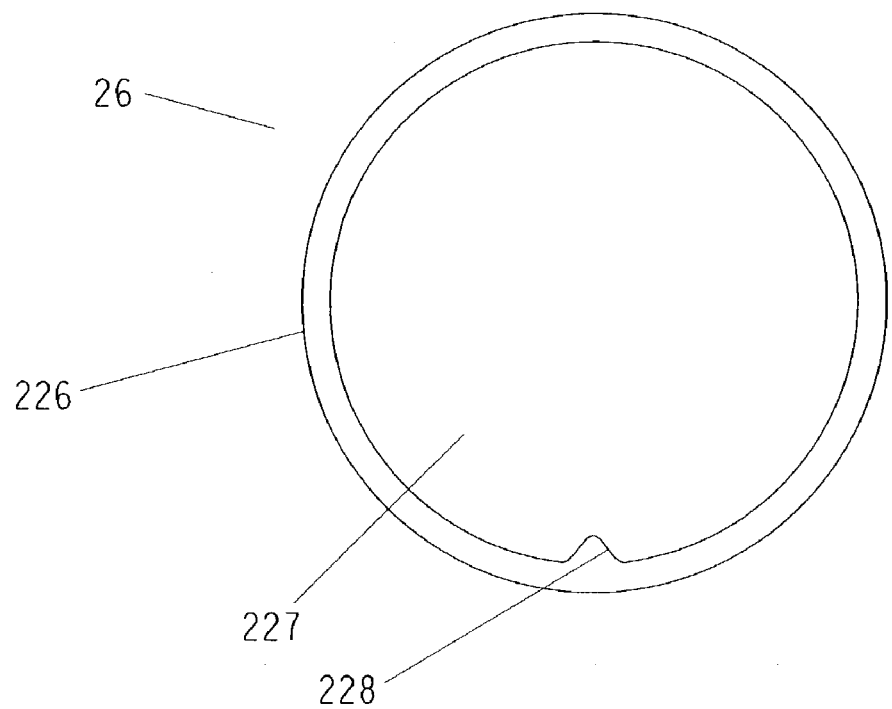
FIG. 5B depicts in cross-sectional form an embodiment of a tube having a bump for use in preferred embodiments of the present invention.

The tubes of the present invention may have a relatively smooth surface, or they may be textured. For example, as shown in FIGS. 5A and 5B, tube 26 has an outer solid portion 126, 226, respectively, and an annular hollow portion 127, 227, respectively. In FIG. 5A, tube 26 is provided with a plurality of fins 128 along its inner diameter, and in FIG. 5B, tube 26 is provided with a single "bump" 228. The fins 128 or bump 228 can be provided along any portion of the tube. For example, in a "U"-shaped tube, the fins 128 and/or bump 228 can be provided on the inlet leg, the outlet leg, or the "U"-shaped portion, or any combination thereof. For a straight through tube design, the fins 128 or bump 228 can be provided along the entire length of the tube, or any portion thereof. The fins, or bumps, can either be straight (parallel to the longitudinal axis of the tube) or "rifled" (fins or bumps spiral progressively along the length of the tube) or of any other desired configuration. In tubes manufactured from conventional metallic alloys, the use of spiral bumps is sold under the trademark MERT by Kubota Metal Corporation. See, for example, the web site having the URL address of http://www.kubota.cojp/infra/sc-j/mert/mert-e.html. It is further contemplated in the practice of the present invention to provide both fins 128 and a bump 228 on the same tube, such as by providing the inlet leg of a "U"-shaped tube with fins and the outlet leg with a bump. In all cases, the purpose of the fins, or bumps, or combinations thereof, is basically to improve heat transfer and thereby allow the furnace reactor tubes to operate at even higher capacities within the constraints of the material from which the furnace tubes are constructed (maximum service temperature) described above.

Accordingly, the present invention provides a process for cracking hydrocarbon feedstocks at a reactor outlet temperature above about 1300° F., preferably above about 1450° F., and more preferably above about 1600° F., and at residence times ranging from about 0.02 s to about 0.50 s, preferably from about 0.04 s to about 0.25 s.

Because the reactor furnace tubes 26 of the present invention are non-nickel containing, almost no catalytic coke is laid down on the inside of the tubes, even at these high temperatures. Additionally, because there is significantly no catalytic coke laid down, and the residence times of the present invention are significantly shorter than those of the prior art, unexpectedly the present inventors have found that formation of pyrolytic coke is also significantly reduced.

The present inventors have found that manufacturing furnace reactor tubes from materials that have high service temperatures and reduce both catalytic and pyrolytic coke enables furnaces to be designed that have better yields, and have fewer tubes, each tube operating at higher capacity. For example, whereas in a furnace for which the reactor tubes are manufactured from conventional nickel-containing material, and the furnace annual production capacity is, for example, 200,000,000 lb/year of ethylene, the furnace might need, for example, 300 tubes, each tube having a residence time of 0.125 s. In contrast thereto, in accordance with the present invention, employing tubes of ODS material, of the same length, for the same capacity furnace, only 150 tubes would be needed, each tube having a residence time of 0.08 s and, by virtue of the shorter residence time, having an improved selectivity, that could reduce the fresh feed consumption by 9,500,000 lb/year. Likewise, for a ceramic tube reactor, of the same length, for the same capacity furnace, only 65 tubes would be needed, each tube having a residence time of 0.065 s and, by virtue of the shorter residence time, having an improved selectivity, that could reduce the fresh feed consumption by a further 9,500,000 lb/year.

Figure 1A:
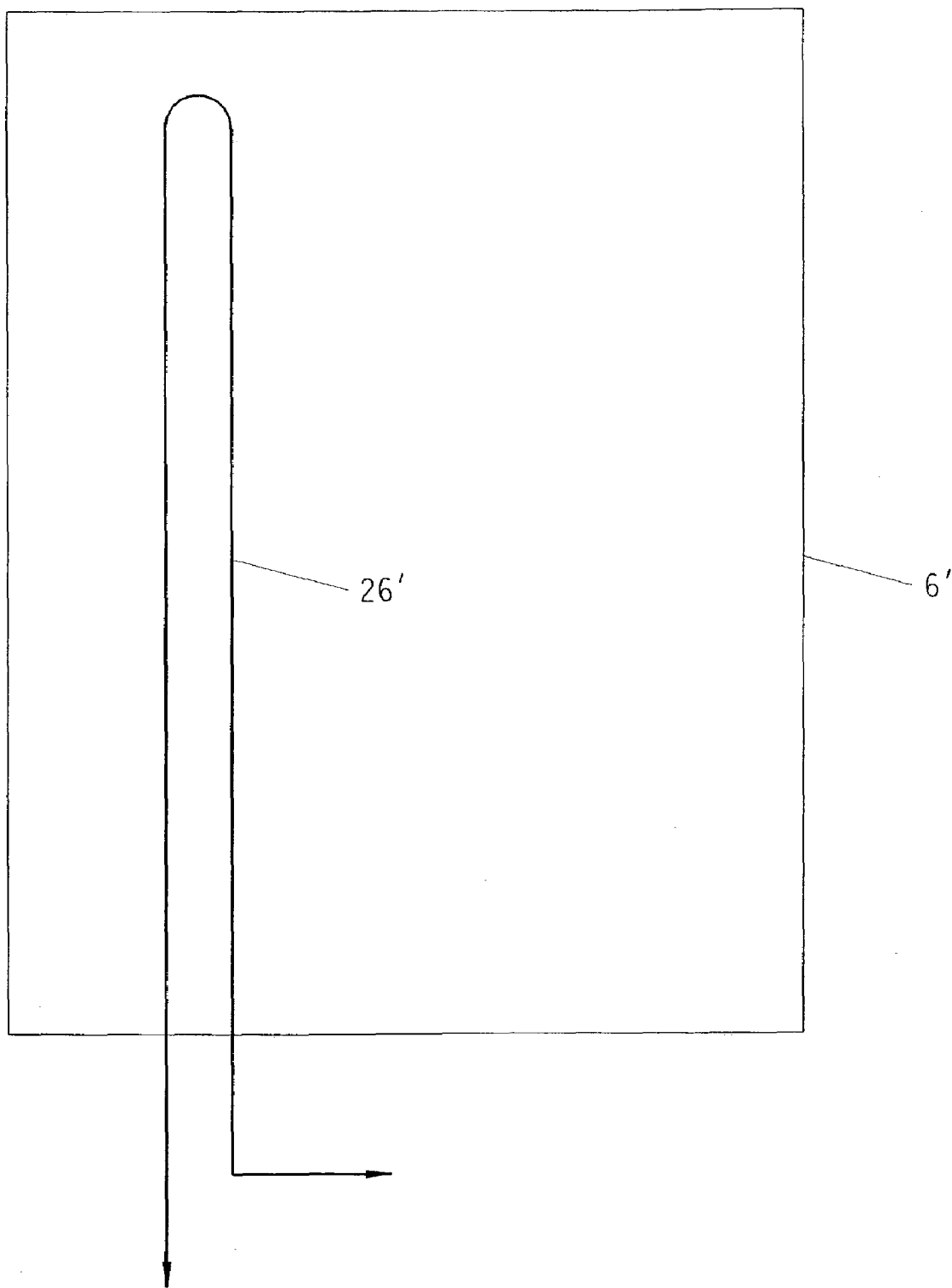
FIGS. 1A and 1B depict preferred embodiments of reactor furnace tube configurations useful in the practice of the present invention.
Figure 1B:
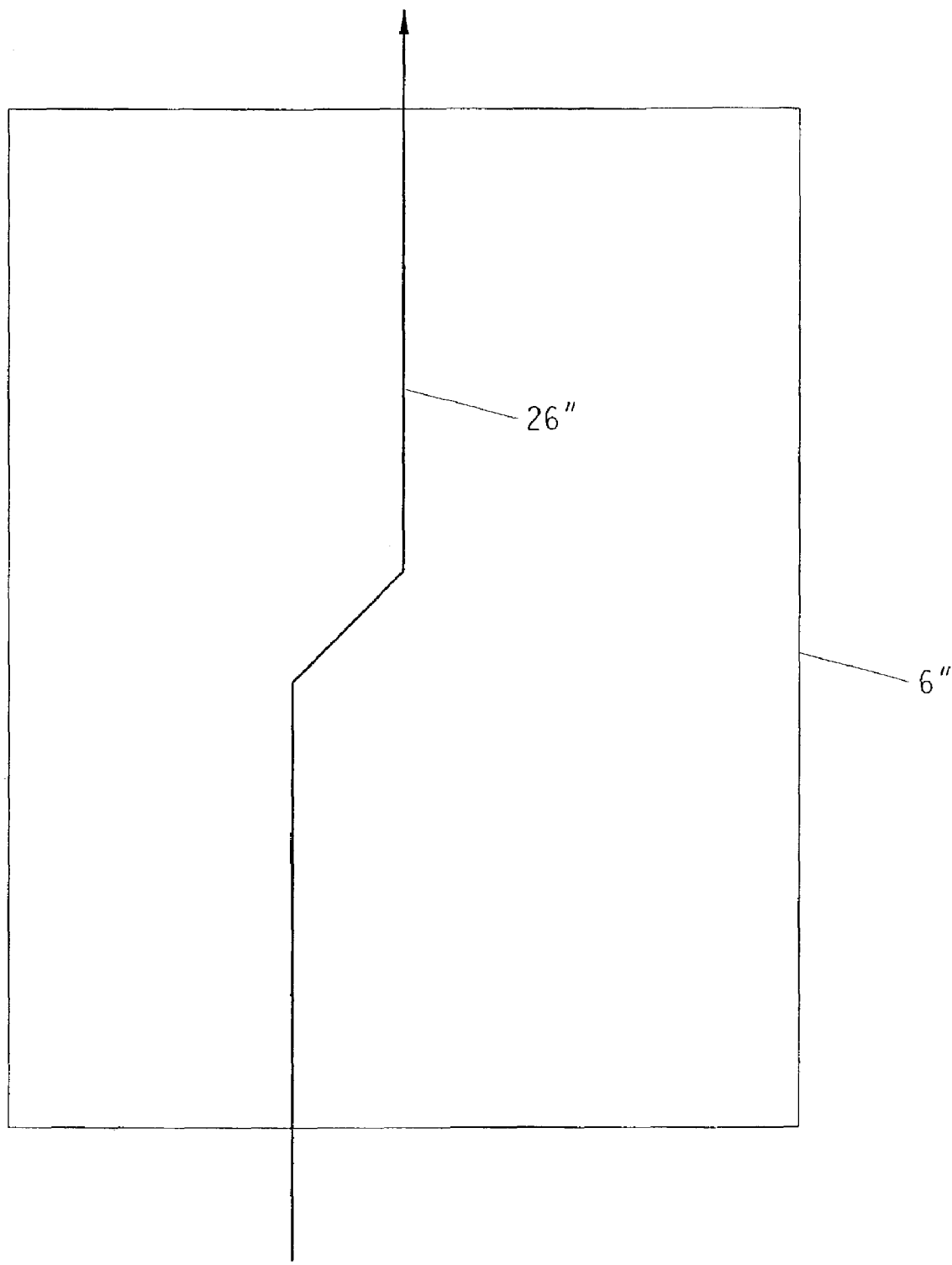

FIG. 1 depicts an embodiment wherein the shape of the reactor furnace tube 26 is a straight one-pass tube. However, the reactor furnace tube may be of any configuration known to those skilled in the art, such as an offset, horizontal or serpentine configuration. FIG. 1A shows a U-shaped reactor furnace tube 26' in a radiant section of a furnace 6', and FIG. 1B shows an offset or bent shaped reactor furnace tube 26" in the radiant section 6" of a furnace. The length of the reactor furnace tube 26 in the depicted shape is preferably from about 20 feet to about 40 feet. However, the length of the reaction line may vary based on its shape, diameter and the furnace capacity.

The reactor furnace tube 26 may also be provided with a means for compensating for thermal tube expansion from the heating in the radiant section of the furnace. Any of the known means for compensating for thermal expansion may be employed in the practice of the present invention, including, but not limited to the use of pigtails as seen in Wallace, U.S. Pat. No. 3,671,198 and offsets as seen in DiNicolantonio et al., U.S. Pat. No. 4,499,055. Of course, other means known to those skilled in the art including, but not limited to, springs and/or counterbalances may also be employed without departing from the present invention.

The inner diameter of the reactor furnace tube may be either constant or swaged. The outer diameter of the depicted reactor furnace tube 26 is preferably from about 1.25" to about 5.00" and most preferably from about 1.75" to about 3.00", with the inner diameter ranging from about 0.30" to about 1.00" less than the outer diameter. However, the diameters and dimensions of the reaction line may vary in ways known to those skilled in the art. In embodiments wherein the reactor furnace tube is swaged, the inner diameter at the reactor entrance can range from about 1.00" to about 2.00" and the inner diameter at the reactor exit can range from about 1.15" to about 2.50", with a smooth transition from one to the other. However, the diameters and dimensions of the reaction line may vary in ways known to those skilled in the art.

Figure 2:
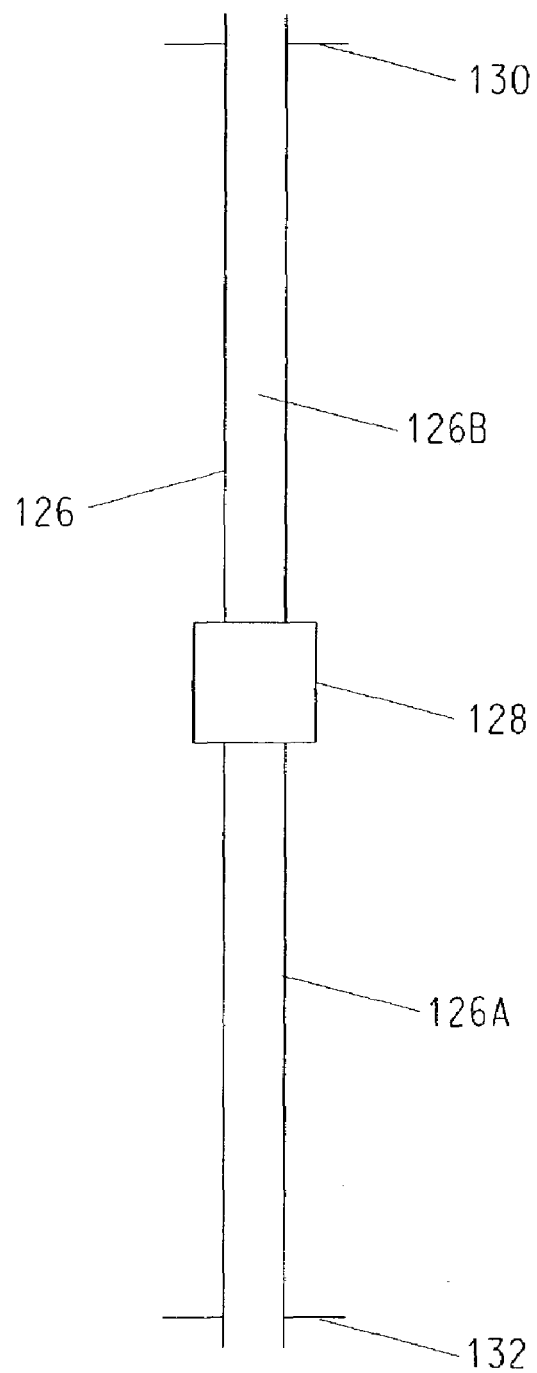
FIG. 2 depicts in schematic form an embodiment of a reactor furnace tube useful in the practice of the present invention.

Depending on the desired length, the reactor furnace tube 26 can be constructed as a single tube or can comprise two or more tubes joined together. In the embodiment depicted in FIG. 2, the reactor furnace tube 126 is shown as two tubes, a lower tube 126A and an upper tube 126B, of approximately equal length joined together at ceramic-to-ceramic joint 128. Of course, in the other embodiments of the present invention, the lengths of the tubes may vary and do not have to be equal or approximately equal. In FIG. 2, the radiant reactor ceiling 130 and floor 132 are also shown.

The ceramic-to-ceramic joint 128 can comprise any of those known to those having ordinary skill in the art. See, for non-limiting examples of sealing means, Bagley, U.S. Pat. No. 3,564,328; Lawler et al., U.S. Pat. No. 3,923,314; Miller, U.S. Pat. No. 3,836,182; Frey et al., U.S. Pat. No. 4,728,128; Kip et al., U.S. Pat. No. 4,773,149; Kipp, U.S. Pat. No. 4,780,160; Mizuhara, U.S. Pat. No. 4,780,161; Mizuhara, U.S. Pat. No. 4,783,229; Schultze et al., U.S. Pat. No. 5,133,577; Holland et al., U.S. Pat. No. 5,152,556; Ward et al., U.S. Pat. No. 5,256,918; Weaver et al., U.S. Pat. No. 5,411,763; and Godziemba-Maliszewski, U.S. Pat. No. 4,784,313.

Figure 3:
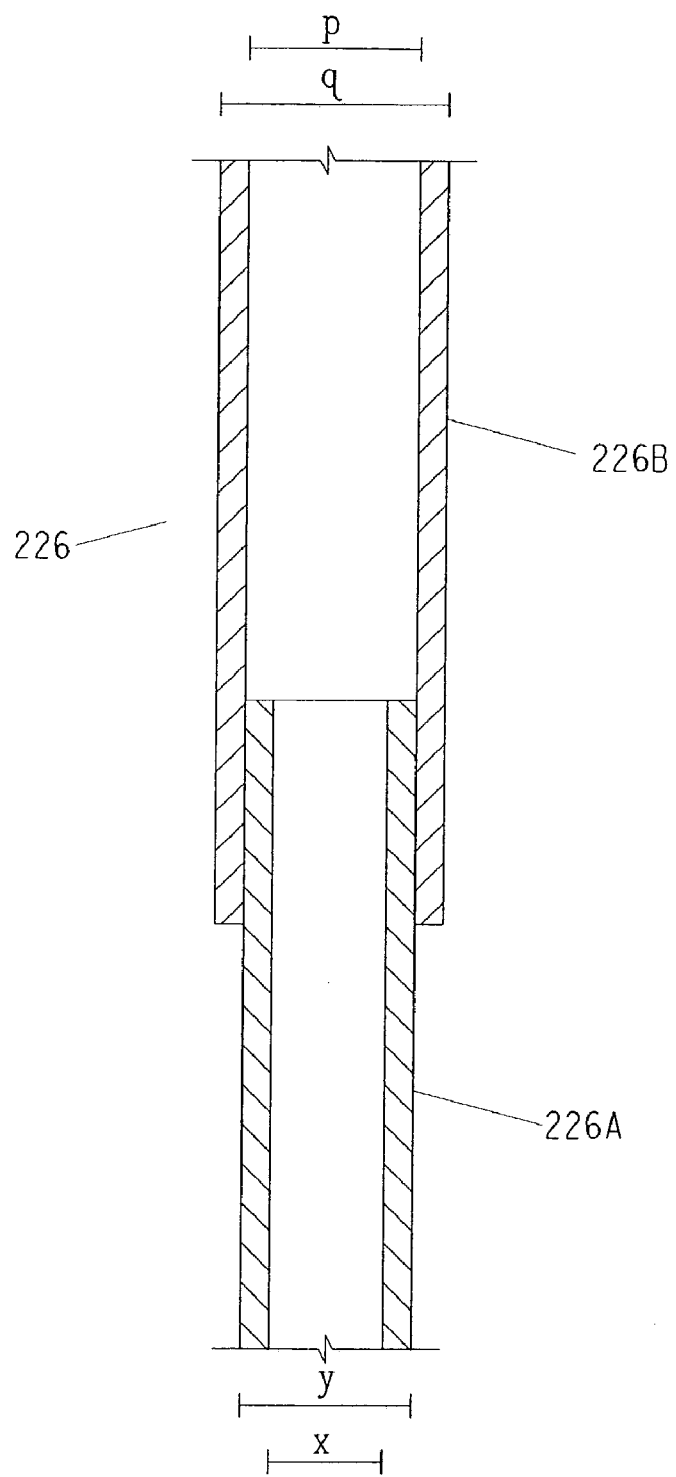
FIG. 3 depicts in schematic form another embodiment of a reactor furnace tube useful in the practice of the present invention.

In another preferred embodiment of the present invention, in order to effect swaging, the two or more tubes that are connected together to form the reactor furnace tube are not of equal diameter. In referring to FIG. 3, reactor furnace tube 226 is comprised of a lower reaction tube 226A having an inner diameter x and an outer diameter y, and an upper reaction tube 226B having an inner diameter p and an outer diameter q. In preferred embodiments, the outer diameter y of lower reaction tube 226A is almost equal to the inner diameter p of upper reaction tube 226B, such that there is a relatively snug fit when lower reaction tube 226A is placed inside upper reaction tube 226B. By using such a design concept, the geometry of 226A and 226B are such as to be particularly convenient for the mechanical design of the joint itself and, at the same time, peculiarly desirable for the performance of the reactor tube, in that the larger diameter of the outlet section of the tube (226B) accommodates the lower molecular weight, lower pressure and higher temperature of the process fluid.

Returning to FIG. 1, as the reactor furnace tube 26 exits the radiant furnace section 6, the material of construction is changed again to a conventional metallic material at joint 29. The joint connections 24 and 29 can be of any type known to those skilled in the art. In general, the prior art describes two methods for connecting ceramic parts to metal parts. These types of methods are the use of metal brazing on the ceramic, and the use of mechanical expedients to compensate for thermal expansion differences, or combinations thereof. Non-limiting examples of the use of brazing are contained in Hoelscher, U.S. Pat. No. 3,620,799; Ebendt et al., U.S. Pat. No. 3,772,766; Ebendt '766; Pessell et al., U.S. Pat. No. 3,862,488; and Bindin, U.S. Pat. No. 4,167,351. Non-limiting examples of mechanical joint arrangements are disclosed in Sedgwick et al., U.S. Pat. No. 3,746,374; Schülke, U.S. Pat. No. 4,349,203; Dockus, U.S. Pat. No. 4,602,731; Napier et al., U.S. Pat. No. 4,902,358; Boecker et al., U.S. Pat. No. 4,610,934; Metcalfe et al., U.S. Pat. No. 4,642,864; von Koch, U.S. Pat. No. 4,702,503; Tsuno et al., U.S. Pat. No. 4,719,075; Ito et al., U.S. Pat. No. 4,723,862; Boecker et al., U.S. Pat. No. 4,871,108; Hunt et al., U.S. Pat. No. 5,013,612; Lasecki et al., U.S. Pat. No. 5,042,847; Mizuhara, U.S. Pat. No. 5,120,374; Li, U.S. Pat. No. 5,161,728; Li, U.S. Pat. No. 5,248,079; Mizuhara, U.S. Pat. No. 5,364,010; Churchill et al., U.S. Pat. No. 5,407,119; and Schultz et al., U.S. Pat. No. 5,163,416.

In the embodiment of the invention in which the reactor furnace tube 26 is manufactured from ODS alloy, rather than ceramic, the joints 24 and 29 can use almost any conventional joining technology, specifically a wide range of welding techniques may be used. In the prior art the design of ODS alloy to ODS alloy joints most often has been addressed, for which the strength of the joint shall be the same as, or similar to the ODS alloy tube. Unfortunately, the main problem with designing such a joint is that the local application of heat that usually is associated with such joining technologies damages the grain structure of the ODS alloy tube in the HAZ (heat affected zone) and causes local weakness. In the case of dissimilar joints 24 and 29, the joint is not required to be any stronger than the conventional metallic alloy from which the line that connects to the furnace reactor tube is joined (e.g., crossover 20). Such a design criterion is relatively easy to meet.

Again referring to FIG. 1, joint 29 connects furnace reactor tube 26 to line 28 (commonly referred to as the transfer line). The transfer line 28 transfers the reaction product gases to quenching means 30, in which the aforesaid reaction product gases are rapidly cooled to a temperature below about 1000° F. to prevent further reaction. Often quenching to much lower temperatures is practiced for the purpose of accomplishing maximum energy efficiency. Quenching means 30 can comprise any of the well-known constructions known to those skilled in the art. See, for example, Woebcke et al., U.S. Pat. No. 5,427,655; Woebcke, U.S. Pat. No. 3,403,722; Woebcke, U.S. Pat. No. 3,910,347; Woebcke, U.S. Pat. No. 4,356,151; and Woebcke, U.S. Pat. No. 5,271,827. After quenching, the cracked products are sent for downstream processing via line 32.

Again referring to FIG. 1, dilution steam, via a line 22 optionally can be added to the feedstock hydrocarbons in accordance with the present invention, and as described in detail above, in amounts generally ranging from about 20% to about 50%. Dilution steam is added in prior art systems to lower the partial pressure of the hydrocarbons to increase the obtainable yields, and for assisting in coke removal from the reactor furnace tubes. Unexpectedly, in designing the present system, the present inventors have found that it is not necessary to add steam to the process. By conducting the reaction in the absence of steam, several important benefits are derived, namely, increased throughput and elimination of the need to remove the water from the reaction products. These additional unexpected benefits make the present invention significantly more attractive from both economic and processing standpoints.

Figure 4:
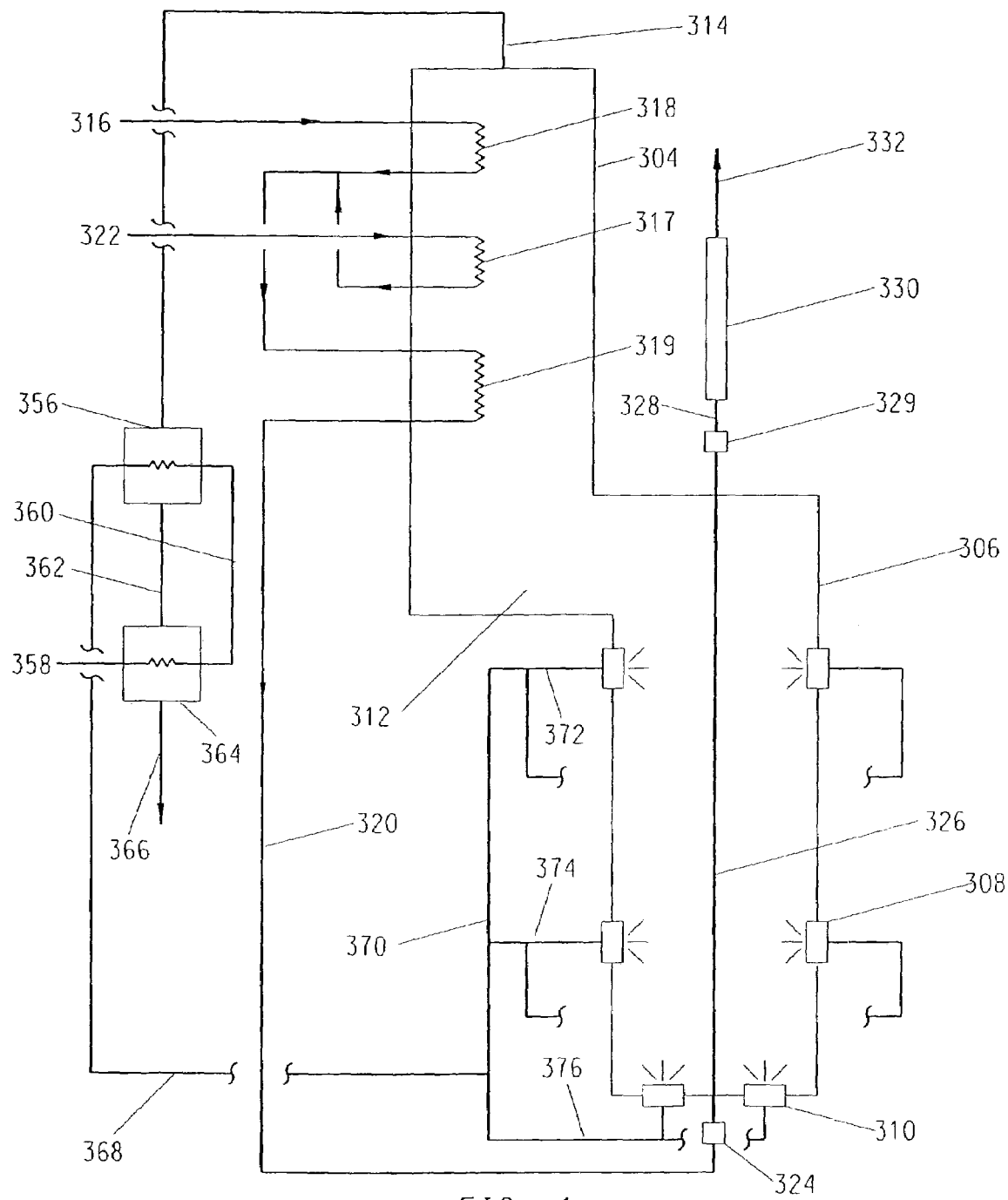
FIG. 4 depicts in schematic form an embodiment of cracking furnace process of the present invention.

In another preferred embodiment of the present invention, the present inventors have found that the higher operating temperatures of the radiant section of the furnace may cause the flue gas temperature exiting the reactor to be significantly higher, and that the radiant burners need to be supplied with preheated air, preheated to such a temperature that the adiabatic flame temperature of the radiant burner is sensibly greater than the flue gas temperature required to supply heat to the reactor furnace tubes that are the subject of this invention. Accordingly, referring to FIG. 4, the present inventors have developed a novel and unobvious system for addressing these issues. In FIG. 4, all similar reference characters correspond to the reference characters in FIG. 1, except that in FIG. 4, the reference characters are in the 300 series. The flue gas exiting the furnace in line 314 has a temperature ranging from about 500° F. to about 1200° F. Since it is well known and commonly practiced in the art that flue gas temperatures should range from about 200° F. to 400° F. before discharging to atmosphere, it is convenient to use the sensible heat of the flue gas to pre-heat the air being supplied to the burners. This preheating and cooling can be conducted in one or more stages. In the embodiment of FIG. 4, two stages are employed. Thus, flue gas in line 314 is directed to indirect heat exchanger 356 where it is indirectly contacted with air previously preheated in indirect heat exchanger 364 from a line 360. Final cooling of flue gas from indirect heat exchanger 356 occurs in indirect heat exchanger 364, which transfers heat indirectly between incoming air in line 358 and partially cooled flue gas in line 362. The partially preheated air from indirect heat exchanger 364 is directed via line 360 to indirect heat exchanger 356 (as described above).

Cooled flue gas is discharged to atmosphere via line or duct 366. The duty split between exchangers 356 and 364 is chosen so that the temperature of the flue gas in line or duct 362 is appropriate for $NO_x$ removal by Selective Catalytic Reduction (SCR) or other means. The preheated air in a line 368, preferably at a temperature ranging from about 400° F. to about 1100° F., is then directed to manifold 370 for feeding wall burners 308 and/or floor burners 310 via lines 372, 374 and 376.

It should be noted that FIGS. 1 and 4 are purely schematic. Details like control systems, forced draft fans, induced draft fans, utility convection bundles within the convection section 304 (for, by way of example, preheating boiler feed water and superheating very high pressure steam) and so on, will be understood by one skilled in the art as necessary and the fact that they are not explicitly described herein does not imply that they are not included in the detailed embodiment of the invention.

The inventors conducted a parametric study using one preferred embodiment of the present invention. The study supports the unexpected conclusion that the advantages of tubes manufactured from new materials that can operate at high temperatures without coke, may result in the tubes having a capacity that is perhaps 2.8 times greater than that of conventional tubes regardless of tube diameter. The study also supports the conclusion that the advantages of ODS tubes may result in the tubes having a capacity that is perhaps 1.6 times greater than that of conventional tubes regardless of tube diameter.

The parametric study was based on a typical Middle Eastern mid-range naphtha being cracked at moderate severity (propylene/ethylene ratio of 0.50 wt/wt), at a typical steam/hydrocarbon ratio of 0.50 wt/wt, and at a typical operating pressure or coil outlet pressure of 26.7 psia (12.0 psig), using 30-foot long reaction tubes of varying diameters. The parametric study determined the effect of varying tube diameter, feed rate and temperature on tube capacity. Table I sets forth the raw data from the study. FIGS. 6-8 set forth the results in chart form.

FIG. 8 depicts the dimensionless hydrocarbon feed rate (%) as a function of maximum tube temperature (° F.). FIG. 8 shows that the maximum temperature of the tube, as a function of feed rate, is almost independent of tube diameter (as the diameter increases, area increases and flux decreases, hence temperature decreases, which is almost offset by the relationship that as diameter increases, the inside film coefficient decreases and hence the temperature increases).

FIG. 7 depicts a relative once through ethylene yield (%) as a function of dimensionless hydrocarbon feed rate for tubes of five different inner diameters ranging from 1.00 inches to 2.00 inches. FIG. 7 reflects that product yield for a tube of any given inner diameter generally increases with the hydrocarbon feed rate. FIG. 7 also reflects that a tube of any given diameter has associated with it an optimum point at which yield does not increase despite increases in the feed rate. For example, the optimum feed rate for a 1.0" diameter coil is about 4 (dimensionless) units; for a 1.25" tube is about 5 units, for a 1.50" tube is about 9 units. FIG. 7 further reflects that the greater the inner diameter of the tube, the greater is the feed rate required to obtain optimum product yield from the tube.

FIG. 6 depicts the relative once through ethylene yield (%) as a function of maximum tube temperature (° F.) for tubes of five different inner diameters ranging from 1.00 inches to 2.00 inches. Although FIG. 6 represents the results as a function of temperature, in fact, temperature should be regarded as a dependent variable. The true independent variable is capacity or feed rate. Hence, for each tube diameter there is an optimum point for the selectivity (highest yield). At temperatures below the optimum, the feed rate is too low and the residence time is too long. At temperatures above the optimum, the feed rate is too high and the pressure drop is too high. FIG. 6 further reflects that the greater the inner diameter of the tube, the greater the temperature required to obtain optimum product yield from the tube and, hence, the greater the feed rate (or capacity). Thus, by operating with tubes of the present invention, the optimum yields can be attained by operating at the higher tube temperatures.

Comparing FIG. 7 with FIG. 8, it can be seen that with current conventional Cr/Ni alloy tubes, the ideal tube capacity is about 5 units, regardless of diameter (in actual practice, this is not true because the Ni in the alloy catalyzes the coke formation, so that either anti-coking technology needs to be practiced or the maximum tube temperature needs to be reduced to 1900° F. and capacity to about 3 units). Utilizing the tubes of the present invention, however, having material limits of up to about 2300° F. (for ODS materials) or up to about 2900° F. (for silicon carbide ceramic tubes), both of which substantially eliminate coke, increases capacity of the coil to 6 units for ODS materials (double the capacity of the conventional alloy tube) and to 14 units for ceramics (or four to five times greater than the conventional alloy tube).

Although it is noted that there are several other more complex design considerations, using a basic example, and comparing a conventional Cr/Ni alloy tube based on a 1.00" tube at a 1900° F. temperature versus a 1.75" ceramic tube at a 2700° F. temperature; the ceramic tube gives 2.5% better ethylene yield and 4.0 times higher capacity.

TABLE I

| I.D. (Inches) | Relative Naphtha Feed | Maximum Tube Temperature (Deg F.) | Relative C$_2$H$_4$ % | Relative Residence Time |
|---|---|---|---|---|
| 1.00 | 1.0 | 1668 | 3.55 | 3.200 |
| 1.00 | 2.0 | 1819 | 6.74 | 1.260 |
| 1.00 | 3.0 | 1928 | 7.76 | 0.680 |
| 1.00 | 4.0 | 2022 | 7.97 | 0.400 |
| 1.00 | 5.0 | 2107 | 7.76 | 0.260 |
| 1.00 | 7.0 | 2261 | 6.74 | 0.120 |
| 1.25 | 1.0 | 1662 | 1.69 | 5.000 |
| 1.25 | 2.0 | 1823 | 5.83 | 2.080 |
| 1.25 | 3.0 | 1941 | 7.59 | 1.140 |
| 1.25 | 4.0 | 2040 | 8.47 | 0.700 |
| 1.25 | 5.0 | 2127 | 8.92 | 0.440 |
| 1.25 | 6.0 | 2207 | 9.13 | 0.280 |
| 1.25 | 7.0 | 2280 | 9.03 | 0.200 |
| 1.25 | 9.0 | 2419 | 8.64 | 0.080 |
| 1.25 | 11.0 | 2548 | 7.94 | 0.000 |
| 1.50 | 1.0 | 1689 | 0.00 | 7.240 |
| 1.50 | 2.0 | 1818 | 4.39 | 3.160 |
| 1.50 | 3.0 | 1941 | 6.50 | 1.820 |
| 1.50 | 4.0 | 2039 | 7.62 | 1.180 |
| 1.50 | 5.0 | 2130 | 8.54 | 0.800 |
| 1.50 | 7.0 | 2268 | 9.41 | 0.380 |
| 1.50 | 9.0 | 2426 | 9.73 | 0.059 |
| 1.50 | 11.0 | 2554 | 9.55 | 0.053 |
| 1.50 | 13.4 | 2698 | 9.31 | 0.049 |
| 1.50 | 15.0 | 2790 | 8.82 | 0.047 |
| 1.75 | 3.0 | 1988 | 5.23 | 2.680 |
| 1.75 | 5.0 | 2196 | 7.66 | 1.280 |
| 1.75 | 7.0 | 2362 | 8.89 | 0.700 |
| 1.75 | 9.0 | 2509 | 9.69 | 0.380 |
| 1.75 | 11.9 | 2699 | 10.15 | 0.140 |
| 1.75 | 13.0 | 2769 | 10.19 | 0.080 |
| 1.75 | 15.0 | 2888 | 10.19 | 0.050 |
| 2.00 | 3.0 | 1997 | 3.93 | 3.680 |
| 2.00 | 5.0 | 2211 | 6.71 | 1.860 |
| 2.00 | 7.0 | 2384 | 8.18 | 1.080 |
| 2.00 | 9.0 | 2535 | 9.13 | 0.660 |
| 2.00 | 11.3 | 2698 | 9.87 | 0.380 |
| 2.00 | 13.0 | 2799 | 10.19 | 0.240 |
| 2.00 | 15.0 | 2917 | 10.43 | 0.056 |

Although the present invention has been described in certain preferred embodiments, all variations obvious to one skilled in the art are intended to fall within the spirit and scope of the invention, including the appended claims. All of the above-referenced patents, patent applications and publications are hereby incorporated by reference in their entirety.

The invention claimed is:

1. A process for selectively cracking a hydrocarbon feedstock into olefinic hydrocarbon products in a radiant fired cracking furnace having reactor furnace tubes and concomitantly reducing coke production on said reactor furnace tubes, said process comprising:

cracking said hydrocarbons in a furnace at a reactor outlet temperature of above about 1300° F. at residence times ranging from about 0.02 s to about 0.08 s in a pyrolysis cracking furnace comprising a plurality of reactor furnace tubes;

wherein said reactor furnace tubes consist of a non-nickel-containing material that can withstand temperatures of at least about 2100° F.;

wherein said reactor furnace tubes have a length of less than 35 feet and an internal diameter ranging from about 1.0 to 2.0 inches; and wherein the amount of coke laid down on said tubes is reduced and the primary products of said selective cracking of said hydrocarbons is olefins and the furnace throughput is increased.

2. A process as defined in claim 1 wherein said reactor furnace tube is constructed of a ceramic material.

3. A process as defined in claim 2 wherein said ceramic material is selected from the group consisting of alpha silicon carbide, reaction bonded silicon carbide, silicon nitride, alumina, and alumina/silicon carbide composites.

4. A process as defined in claim 3 wherein said ceramic material comprises a direct sintered silicon carbide.

5. A process as defined in claim 1 wherein said reactor furnace tube consists essentially of oxide dispersion strengthened ferrous alloy.

6. A process as defined in claim 5 wherein said oxide dispersion strengthened ferrous alloy comprises a rare earth oxide dispersion strengthened ferrous alloy which contains from about 17% to about 26% of Cr by weight and about 2% to about 6% of Al by weight.

7. A process as defined in claim 1 wherein said reactor furnace tube comprises a straight configuration.

8. A process as defined in claim 1 wherein said reactor furnace tube comprises an offset configuration.

9. A process as defined in claim 1 wherein said reactor furnace tube comprises a serpentine configuration.

10. A process as defined in claim 1 wherein said reactor furnace tube is of an essentially constant diameter.

11. A process as defined in claim 1 wherein said reactor furnace tube has a swaged diameter.

12. A process as defined in claim 1 wherein said reactor furnace tube is comprised of two tubes, a lower tube and an upper tube joined together.

13. A process as defined in claim 12 wherein said lower tube has a smaller diameter than said upper tube.

14. A process as defined in claim 1 further comprising adding dilution steam to said hydrocarbon feedstock.

15. A process as defined in claim 1 wherein said reaction temperature is above about 1600° F.

16. A process as defined in claim 15 wherein said reactor furnace tube is constructed of a material comprising a ceramic.

17. A process as defined in claim 15 wherein said furnace is heated by radiant burners that are fed with preheated air.

18. A process as defined in claim 15 wherein said preheated air is obtained by preheating air with a flue gas issuing from said furnace.

19. A process as defined in claim 1 further comprising preheating said hydrocarbon feedstock with flue gas in a convection zone of said furnace.

20. A process as defined in claim 1 wherein said reaction tube is provided with fins or a bump.

21. A process as defined in claim 1 wherein said hydrocarbon feedstock comprises ethane, propane, butane, naphtha, gas oil or vacuum gas oil.

22. A process as defined in claim 21 wherein said process selectively cracks vacuum gas oil, a heavy feedstock or mixtures thereof.

23. A process as defined in claim 21 wherein said process selectively cracks a feedstock comprising ethane to ethylene.

24. A process as defined in claim 1 wherein said feedstock is ethane and said process operates at a conversion ranging from about 85% to about 90%.

25. A process as defined in claim 1 wherein at least one said reactor furnace tube is joined to a tube containing metallic material that is outside said furnace.

26. A process as defined in claim 1 wherein said tube length ranges from about 20 to 35 feet.

27. A process as defined in claim 26 wherein said tube length ranges from about 30 to 35 feet.

* * * * *